_United States Patent_ [19]

Patrichi

[11] 4,196,249

[45] Apr. 1, 1980

[54] SELF LUBRICATING BALL JOINT LINER CHARACTERIZED BY A SURFACE COMPRISING HARD METAL PARTICLES

[75] Inventor: Mihai D. Patrichi, Los Angeles, Calif.

[73] Assignee: Networks Electronic Corp., Chatsworth, Calif.

[21] Appl. No.: 868,196

[22] Filed: Jan. 9, 1978

[51] Int. Cl.$^2$ .......................... B32B 5/28; B32B 5/30; B32B 15/02; F16C 33/24
[52] U.S. Cl. .................................... 428/242; 308/238; 308/DIG. 8; 308/DIG. 9; 403/140; 428/263; 428/328; 428/335; 428/338; 428/339

[58] Field of Search ............... 428/328, 242, 263, 335, 428/338, 339; 308/DIG. 8, DIG. 9, 238; 403/140

[56] References Cited

U.S. PATENT DOCUMENTS 3,594,049   7/1971   Turner ................................. 428/328

_Primary Examiner_—J. C. Cannon

[57] ABSTRACT

A finely divided hard metal powder of low thermal expansion and high corrosion and acid resistance, intimately mixed with a colloidal dispersion of tetrafluoroethylene and a thermoplastic, thermosetting adhesive, is applied to one side of a backing member of woven, high tensile strength material in several applications so as to saturate the material to a substantial depth, providing a long-lasting wear surface.

10 Claims, 5 Drawing Figures

SELF LUBRICATING BALL JOINT LINER CHARACTERIZED BY A SURFACE COMPRISING HARD METAL PARTICLES

BACKGROUND OF THE INVENTION

In the prior art, there are a number of disclosures of bearing members utilizing tetrafluoroethylene to provide a low-friction bearing surface. For example:

Peter H. Turner U.S. Pat. No. 3,594,049 discloses a bearing liner including a mixture of polytetrafluoroethylene (hereinafter referred to by the initials PTFE) in finely powdered form, and an adhesive (e.g. of phenolic base) in a low friction layer on a backing member of woven material, and states that a minor proportion of a metal powder additive such as bronze, babbitt or lead, may be included in the low friction layer.

Charles S. White U.S. Pat. No. 3,458,223 discloses the use of PTFE fibers on the surface of a spherically shaped bearing element including an annular composite cloth insert having the PTFE fibers in mated slidable engagement with an inner bearing element.

Andrews U.S. Pat. No. 3,231,460 discloses the use of PTFE as an impregnant on a mineral fiber (e.g. asbestos) sheet. Other such patents are in the prior art.

None of the above mentioned patents disclose the use of finely divided hard metal powder of low thermal expansion and high corrosion and acid resistance.

OBJECTS OF THE INVENTION

The invention has as its general object to provide a bearing liner combining low friction characteristics with long wear life and extremely low surface wear.

A particular object is to provide a bearing liner having self-lubricating characteristics.

Another object is to provide a bearing surface for sliding or rotating motion against a coacting surface, in which a proportion of hard metal in a finely divided state, assists in obtaining the objective of long wear life combined with extremely low surface wear.

A further object is to provide a bearing liner in which the above mentioned characteristics are attained by coating a sheet of woven material with a dispersion of an adhesive and a solvent and a low-friction material, along with a percentage of fine, hard metal filler powder.

IN THE DRAWINGS

FIG. 1a showing the material after calendering and application of the wear coat;

DETAILED DESCRIPTION

Figure 4:
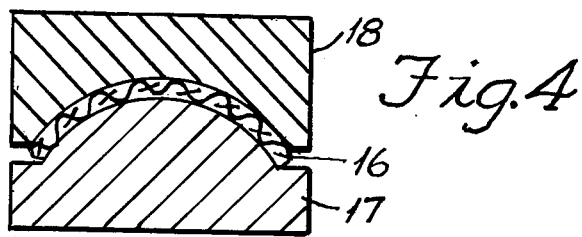
FIG. 4 is a cross-sectional view showing the molding of the bearing liner.

Referring now to the drawing in detail, I have used the reference numeral 5 to indicate the woven fabric backing member, of very high tensile and compressive strength, not affected materially by acids or alkalies, and capable of withstanding temperatures up to 700° F. Being a woven material, it has openings, pores and cavities providing a porous surface 6. Peaks 7 are at the high points of the material, and cavities 8 are defined between peaks 7. Pores 6 extend through the fabric, and are filled with the adhesive and low-friction material which also fills the cavities 8. One particular material that may be used, for the backing member, is Aramid, by Du Pont. This material has the qualities desired for the backing member. However, the invention is not to be considered as restricted to the use of this particular material. Preferably, a synthetic material is used in order to attain the combination of qualities referred to above.

The woven material 5 is treated with several applications of adhesive/solvent, metal powder filler and low friction material as follows:

The adhesive is a thermo-plastic, thermosetting compound adapted for solution in a suitable solvent. This material will also be referred to as a binder. For the low friction material tetrafluoroethylene resin is useful for its low friction characteristic, its durability, and its extreme resistance to heat and chemicals, but application involves difficulties which have been overcome by mixing it with the binder and metal powder in a ball mill, thus producing a good dispersion and a very smooth, uniform mixture which can be easily applied by means of spraying. The tetrafluoroethylene low friction material (hereinafter referred to by the trademark Teflon is in powdered form, its grain size not exceeding five microns.

The metal powder utilized by the invention is not a "soft" metal, contrary to all expectations, but a hard metal such as tungsten or tungsten alloy or wolfram (a tungstate of iron and manganese). Tungsten is preferred. It is utilized in the form of a very fine powder, as fine as 0.8 micron grain size. Its concentration in the mixture of ingredients is preferably between 1% and 2% of the total. At this concentration, test results show the following:

Wear life: The anti-friction mixture exhibits 0.002 inch wear at 40,000 P.S.I. (pounds per square inch) over 30,000 cycles.

Heat resistance: Minimum 350° F.

Peel test: The anti-friction material exhibits a peel strength of 10 lbs/inch minimum.

$TiO_2$ (titanium oxide) is used as an extender for the metal powder in the combination, and provides a homogeneous dispersion of the metal powder in the mixture.

Referring again to the drawing, in a first step of applying the above described materials to the woven fabric backing member 5, a solution comprising a mixture of the adhesive and a solvent blended at a specific ratio to a homogeneous solution, is applied to the backing member in a manner to saturate the same to a depth indicated at 10. The saturated material is then air or force dried at a temperature not exceeding 200° F. Gravity is utilized in obtaining penetration of the fabric. Saturation to a depth of approximately 50% of material thickness is thus obtained.

A mixture of the adhesive/solvent solution and a tungsten metal filler such as that previously described, is then dispersed onto the backing member in a coating approximately 25% of material thickness, indicated at 11 in the drawing. The material is thus saturated to a depth about 75% of material thickness, as indicated at 14 in the drawing. This step may be repeated in order to achieve maximum thorough saturation. Following the application of each such coating, the material is air or force dried at a temperature not exceeding 200° F.

In the next step, a mixture containing the adhesive/solvent solution, the tungsten metal filler, and the low-friction Teflon powder referred to above, is applied to the backing member in a coating indicated at 12 in the drawing. This coating likewise has a thickness of about 25% of material thickness. The coated material is then calendered under a pressure of approximately 2000 lbs. per square inch, after first being air or force dried at a temperature not exceeding 200° F. Under the calendering step, the material is brought to a specified thickness, uniform throughout its area. Numeral 15 indicates the thickness at this point.

Following the calendering step, there is dispersed onto the backing member, more of the adhesive/solvent, tungsten, Teflon powder mixture, producing a coating, indicated at 13, which protrudes not more than 0.002 inches above the peaks 7 of the backing member.

Figure 1:
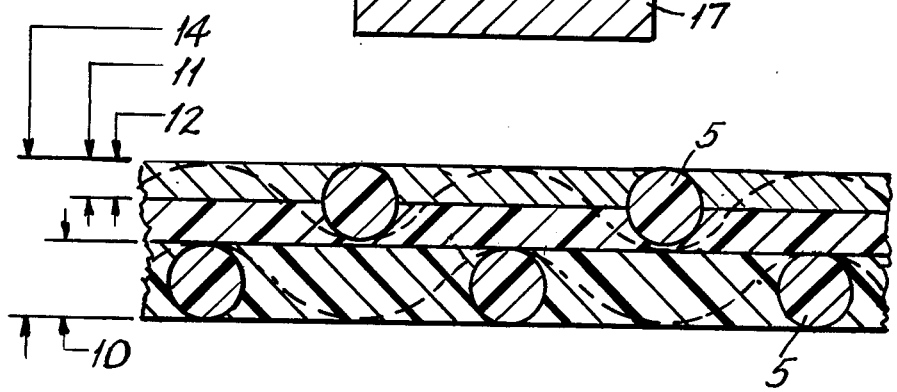
FIGS. 1 and 1a are highly magnified cross-sections of a small portion of a bearing liner embodying the invention, FIG. 1 showing the material before deposit of the bearing coating and before the calendering step.
Figure 1A:
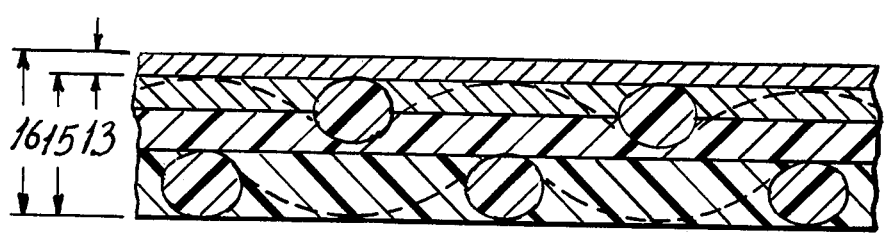
Figure 2:
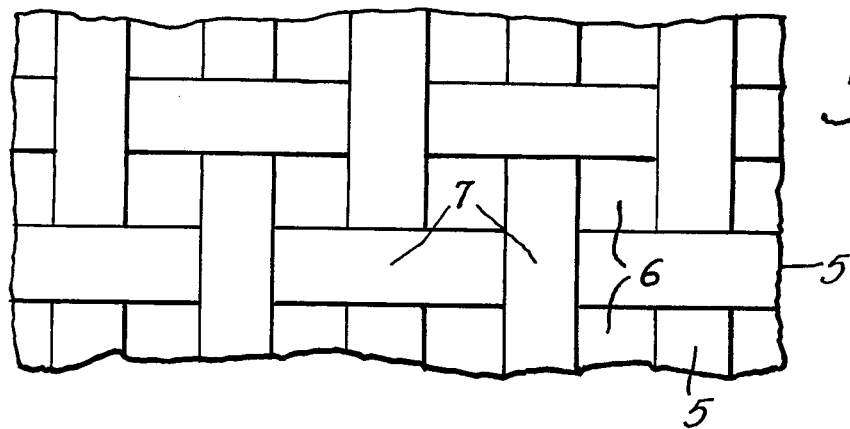
FIG. 2 is a plan view of the same with the top coating removed.
Figure 3:
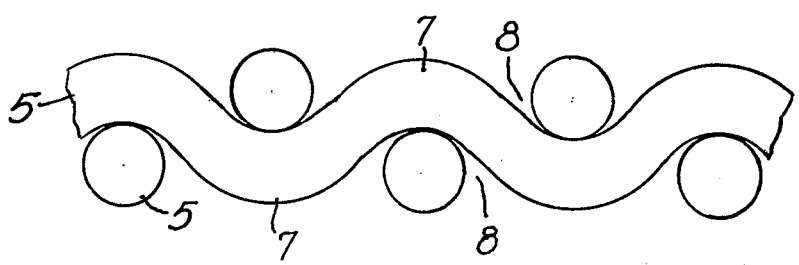
FIG. 3 is an edge view of the woven backing.

The coated material is then calendered at a pressure up to 4000 pounds per square inch, thereby obtaining a uniform specific thickness indicated at 16 in FIG. 1a. The material then has a highly glossy, smooth finish and enhanced compressive strength and low coefficient of friction and improved wear life, eliminating "cold flow" under "point contact" conditions.

The following table shows a specimen of some of the formulae used in a series of tests conducted during research on the invention:

| MATERIALS | SAMPLES | | | | | | |
|---|---|---|---|---|---|---|---|
| | 1 | 2 | 3 | 4 | 5 | 6 | 7 |
| Tungsten | 1 | 1 | 2.5 | 2.5 | 3 | 8 | — |
| TiO₂ | — | 2 | 3 | — | — | — | — |
| Teflon | 25 | 24 | 21.5 | 24.5 | 24 | — | 22 |
| Binder | 74 | 74 | 73 | 73 | 73 | 92 | 78 |

When tungsten powder was eliminated completely, the wear occurred rapidly, before reaching even 10,000 cycles. On a high concentration of tungsten powder (6-8%) the material exhibited a very good resistance, but for a very short number of cycles. At a concentration between 1% and 2% of tungsten powder, the best results were obtained, as previously indicated.

Referring now to FIG. 4, the previously treated material 16 may be cured under heat and pressure for a specific period of time, in a mold including male and female elements 17 and 18 respectively, resulting in a self-lubricating pad of meniscus shape suitable, for example, for surgical insertion into a human knee-joint (Ultra High Molecular Weight Polyethylene is to replace TFE) to overcome arthritic condition.

The lubricating material may be cut into various shapes and sizes to suit particular configurations, and then molded or bonded to fit a given joint structure. Male or female configurations may be utilized to present the low-friction, self-lubricating surface of the material on the convex or concave surface of the molded material, as desired.

I claim as my invention:

1. A low friction bearing liner of high wear life, comprising:
   a backing member comprising woven fabric of high tensile and compressive strength;
   a body of plastic material permeating said fabric, said plastic material comprising:
   a minor percentage of powdered, very hard material in a coating providing the wear surface of said material;
   a higher percentage of powdered tetrafluoroethylene embodied in said coating;
   and a major proportion of binder material intimately mixed with said powdered materials;
   said wear surface coating having a self-lubricating, highly glossy, smooth finish.

2. A bearing liner as defined in claim 1, wherein said hard material is selected from the group including tungsten, tungsten alloys, and titanium oxide.

3. A bearing liner as defined in claim 1, wherein said hard material is selected from the group including tungsten and tungsten alloys.

4. A bearing liner as defined in claim 1, wherein said hard material consists of tungsten.

5. A bearing liner as defined in claim 1, wherein said hard material consists of tungsten of a grain size not exceeding five microns.

6. A bearing liner as defined in claim 1, wherein said hard material consists of powdered tungsten in a percentage between 2% and 1% of the total composition, of a grain size not exceeding five microns.

7. A bearing liner as defined in claim 1, having a wear life equivalent to 0.0020 inch wear under a pressure of 40,000 pounds per square inch, over 30,000 cycles of movement.

8. A bearing liner as defined in claim 1, calendered under a pressure up to 4000 pounds per square inch.

9. A bearing liner as defined in claim 1, having a calendered wear surface protruding not more than 0.0020 inches above the peaks of the fabric.

10. A bearing liner as defined in claim 1, wherein said backing member is not materially affected by acids or alkalies, and capable of withstanding temperatures up to 500 degrees fahrenheit.

* * * * *